United States Patent
Hermansson et al.

(10) Patent No.: US 6,616,648 B2
(45) Date of Patent: Sep. 9, 2003

(54) ABSORBENT ARTICLE HAVING V-SHAPED ELASTIC ATTACHED TO BACKSHEET

(75) Inventors: Kent Hermansson, Västra Frölunda (SE); Kenneth Strannemalm, Floda (SE); Katharina Karlsson, Härryda (SE); Solgun Drevik, Mölnlycke (SE)

(73) Assignee: SCA Hygiene Products AB, Gothenburg (SE)

(*) Notice: Subject to any disclaimer, the term of this patent is extended or adjusted under 35 U.S.C. 154(b) by 0 days.

(21) Appl. No.: 09/820,686

(22) Filed: Mar. 30, 2001

(65) Prior Publication Data
US 2002/0010455 A1 Jan. 24, 2002

Related U.S. Application Data
(60) Provisional application No. 60/201,315, filed on May 2, 2000.

(30) Foreign Application Priority Data
Mar. 31, 2000 (SE) .............................................. 0001177

(51) Int. Cl.⁷ .............................................. A61F 131/15
(52) U.S. Cl. ..................... 604/385.27; 604/385.23; 604/385.3; 604/385.22; 604/385.21; 604/385.2; 604/385.24; 604/385.27; 604/385.31; 604/380; 604/379; 604/385.01
(58) Field of Search ....................... 604/385.26, 385.22, 604/385.24, 385.27, 385.31, 380, 379, 385.01

(56) References Cited

U.S. PATENT DOCUMENTS

| | | |
|---|---|---|
| 4,229,835 A | 10/1980 | Shaw |
| 4,319,572 A | 3/1982 | Widlund et al. |
| 4,892,536 A | 1/1990 | DesMarais et al. ..... 604/385.27 |
| 4,897,084 A | 1/1990 | Ternstrom et al. ..... 604/385.27 |
| 5,514,120 A | 5/1996 | Johnston et al. ............ 604/378 |
| 6,372,954 B1 | 4/2002 | Johnston et al. ............ 604/378 |
| 6,413,248 B1 | 7/2002 | Mizutani ............... 604/385.17 |
| 6,486,379 B1 | 11/2002 | Chen et al. ................. 604/378 |
| 6,492,574 B1 | 12/2002 | Chen et al. ................. 604/378 |
| 6,503,233 B1 | 1/2003 | Chen et al. ............ 604/385.01 |

FOREIGN PATENT DOCUMENTS

| | | | |
|---|---|---|---|
| EP | 963749 A2 | 12/1999 | .......... A61F/13/15 |
| WO | 90/04374 | 5/1990 | |
| WO | 95/13772 | 5/1995 | |

*Primary Examiner*—John J. Calvert
*Assistant Examiner*—Angela J Grayson
(74) *Attorney, Agent, or Firm*—Burns, Doane, Swecker & Mathis, L.L.P.

(57) ABSTRACT

Absorbent article such as a diaper and an incontinence guard comprising a liquid permeable topsheet (2), a liquid impermeable backsheet (3) and an absorbent body (4) enclosed therebetween, said article having a front portion (5), a rear portion (6) and a crotch portion (7), therebetween, whereby the front and rear portion exhibits side flaps (8, 9), which are intended to attach the article to a pantlike shape around the waist of the user. The article has at least one pre-stressed elastic means (11a) and at least attached to the back sheet, that said first elastic means (11a) is brought in an essentially V-shaped pattern having the peak of the pattern located to a first point (13) being essentially located on a imagined longitudinal center line (12) in said crotch portion (7) and that the V-shaped elastic means (11a) diverge in the direction from said longitudinal center line (12) toward the front portion (5).

15 Claims, 3 Drawing Sheets

ABSORBENT ARTICLE HAVING V-SHAPED ELASTIC ATTACHED TO BACKSHEET

This application claims priority under 35 U.S.C. §§119 and/or 365 to Swedish Application No. 0001177-5 filed in Sweden on Mar, 31, 2000 and to U.S. Provisional Application No. 60/201,315, filed on May 2, 2000, the entire contents of which are hereby incorporated by reference.

TECHNICAL FIELD

The present invention relates to an absorbent article such as a diaper and an incontinence guard comprising a liquid permeable topsheet, a liquid impermeable backsheet and an absorbent body enclosed therebetween, said article having a front portion, a rear portion and a crotch portion therebetween, whereby the front and rear portion exhibits side flaps, which are intended to attach the article together to a pantlike shape around the waist of the user. The article comprises at least one elastic means, which is preferably arranged between the absorption body and the backsheet.

THE BACKGROUND OF THE INVENTION

Diapers and incontinence guards for incontinent adults usually exhibit a garment portion holding an absorption body in place against the user's body and attachment means, which hold the garment portion in place also when the user is moving.

It is previously known that diapers and incontinence guards for adults are formed, as to form a "basin" in the crotch portion, which can receive the liquid before it is being sucked into the absorbing material. This diaper may be experienced as being unwieldy and uncomfortable for certain persons depending on the body construction. Today's absorption materials usually have such high and fast absorbing properties that the basin construction not always is necessary, since the liquid penetrates the absorbent body at such speed that leakage is avoided. It would therefore be desirable to provide a diaper and an incontinence guard for adults having an improved fit giving the best possible comfort to the wearer and also seals properly against the groins to prevent possible leakage.

U.S. Pat. No 4,229,835 discloses a panty for sport activities which is provided with an Y-shaped elastic support ribbon at the rear portion of the panty. This gives a lifting support for the bottom, but does not lead to an increased sealing against the groins. The object of this panty is to provide an increased comfort and protect the crotch region of the wearer at activities which require long term sitting, for example at a bicycle saddle, a riding saddle or the like. Therefore, an absorbent article is not the issue, whose task is to absorb body liquids and where the leakage security is one of the main objects.

WO 90/04374 discloses a diaper having central located elastic, for the adoption to the body. However, the elastic is not connected to the end portions of the diaper whereby an effective sealing against the groins not is obtained.

EP 729 329 discloses a leg elastic, which is directly connected to a waist belt for a better fit. However, the localisation of the elastic means provides a totally different fit than the present invention.

SUMMARY OF THE INVENTION

The object of the present invention is to provide a diaper or an incontinence guard for adults which has an improved fit which gives the best possible comfort for the wearer and also seals properly against the groins to prevent possible leakage.

This object is being solved through the features, which are given in the characterising portion of claim 1. Further features are evident from the depending claims and in the following description.

BRIEF DESCRIPTION OF THE DRAWINGS

The invention will in the following be closer described with reference to a couple of embodiments shown on the enclosed drawings.

DETAILED DESCRIPTION OF THE INVENTION

Figure 1:
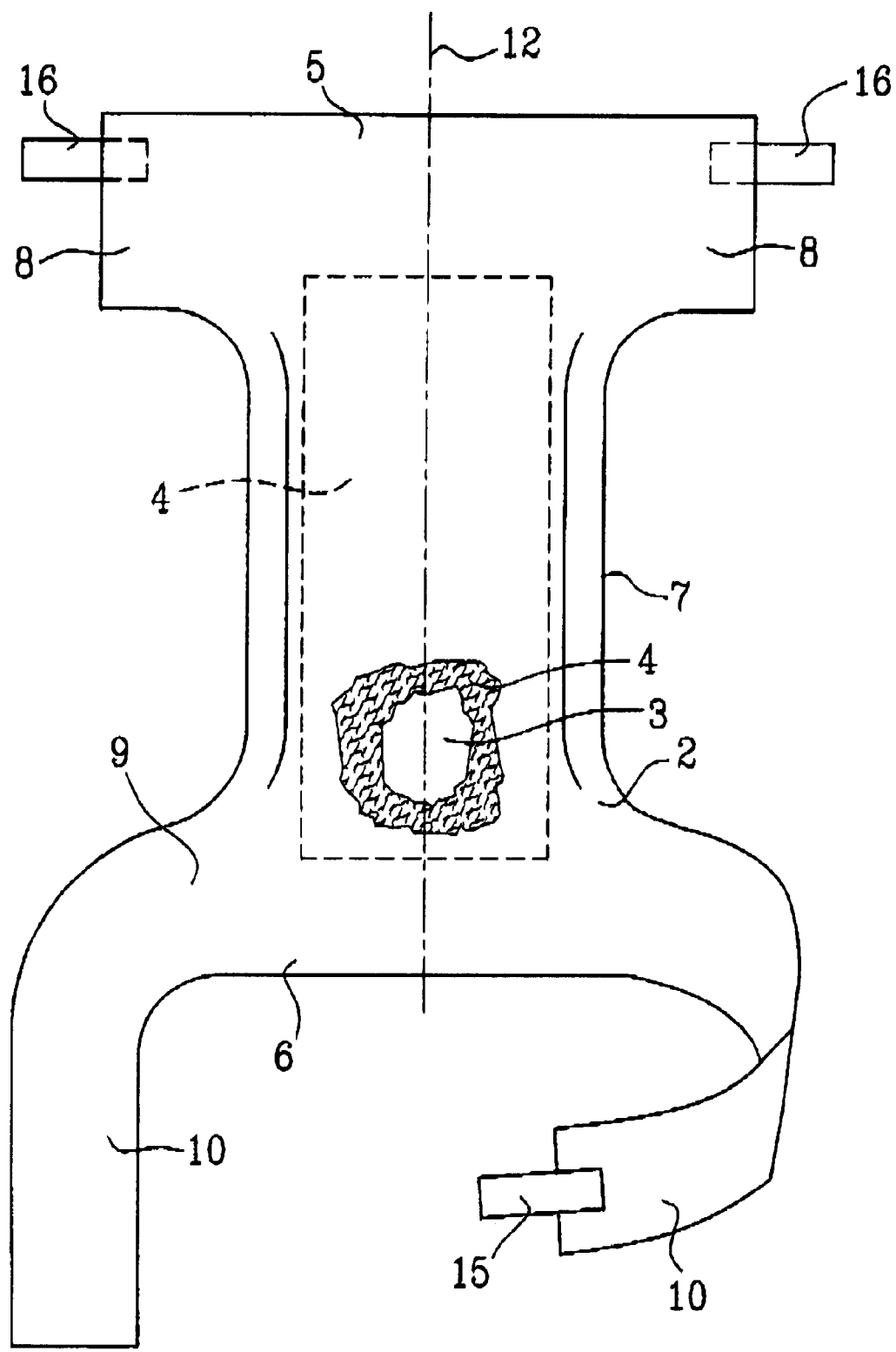
FIG. 1 shows schematically a view in perspective from above of a diaper or incontinence guard according to the invention.

The drawings show a couple of embodiments of diapers or incontinence guards 1, comprising a liquid impermeable back sheet 2, a liquid permeable topsheet 3 and an absorbent body 4 enclosed therebetween. The liquid permeable topsheet 3 may consist of a non-woven material, e.g. a spunbond material from continuos filaments, a meltblown material or a bonded carded fibrous web. The liquid impermeable backsheet 2 may consist of a plastic film, a non-woven material coated with a liquid impervious material or a hydrophobic nonwoven material, which resists liquid penetration.

The backsheet 2 and the topsheet 3 have a somewhat larger extension in the plane than the absorbent body 4 and extend beyond the edges of this. The layers 2 and 3 are mutually connected within the projecting portions, for example through joining using adhesive or welding using heat or ultra sonic.

The absorption body 4 may be of any conventional kind. Examples of common absorption material are cellulosic fluff pulp, tissue layers, highly absorbent polymers (so-called superabsorbents), absorbent foam materials, absorbent non-woven materials or the like. It is common to combine cellulosic fluff pulp with superabsorbents in an absorbent body. It is also common to use absorbent bodies comprising layers of different materials having different properties with respect to liquid acquisition capacity, liquid distribution capacity and storage capacity. It is well known to the person skilled in the art and does therefore not have to be described in detail. The thin absorbent bodies, which are common in for instance baby diapers and incontinence guards, often consists of an compressed mixed or layered structure of cellulosic fluff pulp and superabsorbent.

Figure 2:
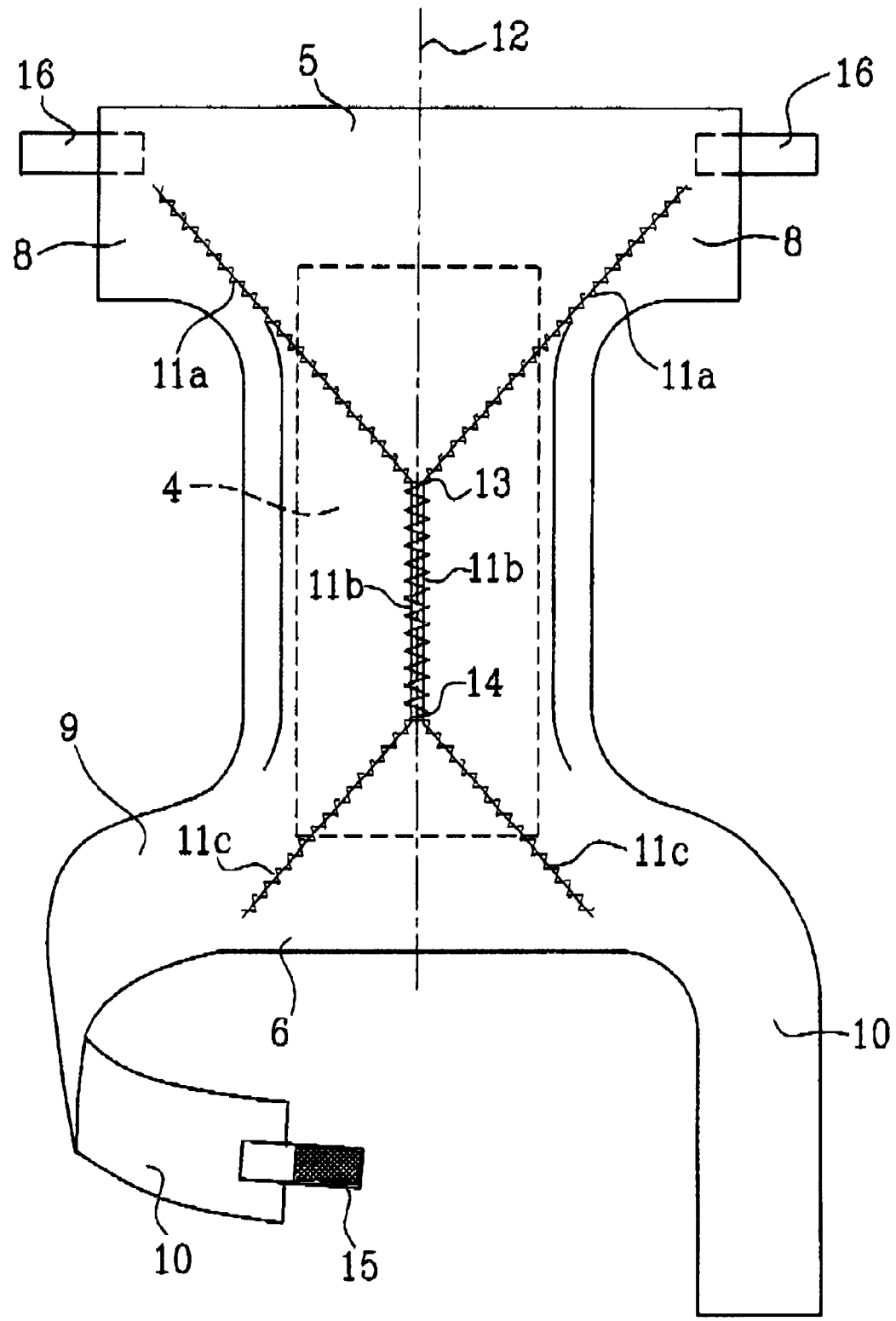
FIG. 2 shows the diaper in FIG. 1 from above designed as a belt diaper.

The diaper/incontinence guard are intended to enclose the lower part of the wearer's trunk like a pair of absorbent pants. It comprises a front portion 5, intended during use to be worn on the front part of the user, a rear portion 6, intended during use to be worn on the rear part of the user, and a more narrow crotch portion 7 located between the font and rear portion, which are intended to be worn in the crotch part of the user between the legs. The front portion 5 exhibits side flaps 8, which can be provided with a kind of fastening means 16, such as adhesive tape portions or hooks and loops fasteners. The rear portion 6 is also provided with side flaps 9, which in the embodiment shown in FIGS. 1 and 2 are extended with a pair of belt parts 10, whereof at least one at its end portion are provided with a fastening means 15, such as adhesive tape portions or hooks and loops fastener. The belt parts 10 are intended to be attached in front of the waist of the wearer by means of fastening means 15. The front portion 5 are then attached to the belt parts 10 by means of fastening means 16 at the side flaps 8 of the front parts.

Figure 3:
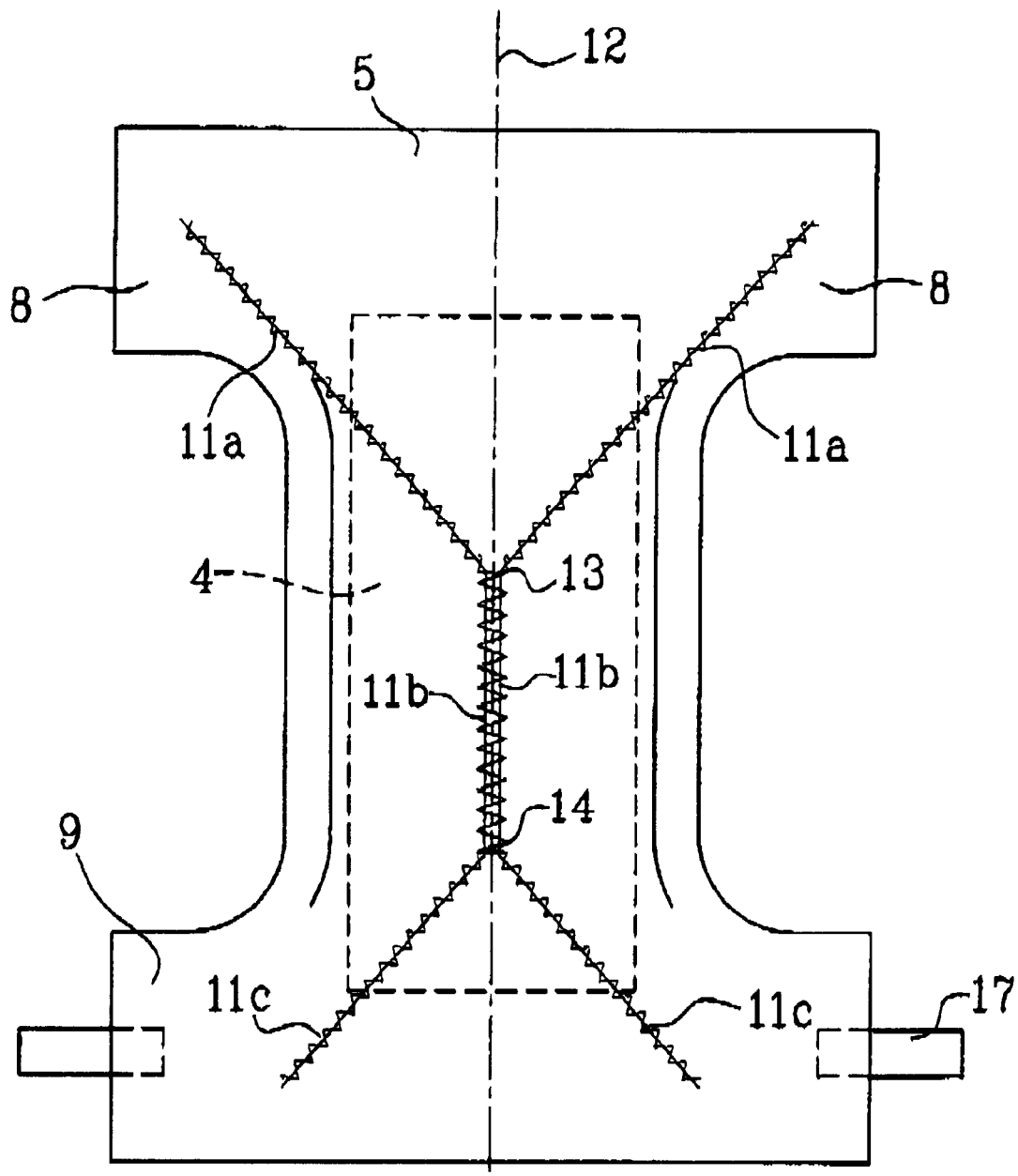
FIG. 3 shows the diaper according to the invention from above designed as a usually so-called all-in-one diaper.

In one embodiment the diaper has at least one first pre-stressed elastic means 11a a arranged preferably between the absorption body 4 and the liquid impermeable back sheet material 2 and is attached at least to the back sheet material 2. The elastic means 11a is arranged in an essentially V-shaped pattern having the peak of the pattern located to a point 13 essentially located on the longitudinal centre line 12 of the article on said crotch region 7. The ends of the V-shaped pattern extend towards the side flaps 8 of the front portion 5. This gives a sealing of the diaper against the groins of the wearer. The article may be a so called belt diaper, as shown in FIGS. 1 and 2, a common so-called all-in one diaper as shown in FIG. 3 or a pant diaper (not shown), in which the side flaps of the front and rear portion are attached to each other so that the diaper has a pantlike form already before usage.

As mentioned above the liquid permeable topsheet 2 and the liquid impermeable backsheet 3 extend beyond the edges of the absorbent body 4, whereby parts of the front portion as well as the rear portion 5, 6 and also the side flaps 8, 9, consist of such projecting and mutually joined portions of the topsheet and the backsheet 2 and 3 outside the absorbent body 4. The diverging ends of the first V-shaped elastic means 11a extend into said projecting portions and are attached between the topsheet 2 and the backsheet 3.

In the case of a belt diaper the diverging ends of the V-shaped elastic means 11a extend adjacent to or even connect to the attachment means 16, which are located on the side flaps 8 of the front portion 5 and are intended to be attached to the belt portions 10. Hereby is a stretching of the elastic means 11a achieved when the diaper is attached together at the application on the user by means of attachment means 16.

In the case of a all-in-one diaper, where the attachment means preferably are located on the side flaps 9 on the rear portion, the elastic means 11 extend in the direction towards the upper edge of the front portion 5. In the case of a pant diaper, having no attachment means, the elastic means 11 also extend in the direction towards the upper edge of the front portion 5.

According to a preferred embodiment a second elastic means 11b is arranged starting from the peak of the first V-shaped means 11a and extend further along the longitudinal centre line 12 in the crotch portion in the direction towards the rear portion 6. Also the second elastic means 11b is preferably arranged between the backsheet 3 and the absorbent body 4 and are at least attached to the backsheet 3. This leads to a lifting of the centre portion of the crotch portion 7 against the crotch region of the wearer, which brings the absorbent body in contact with the wearer leading to a rapid and effective absorption of the liquid.

Further, there is preferably a third elastic means 11c is brought in a second essentially V-shaped pattern. The peak of the pattern is located to a point 14 at the longitudinal centre line 12 on the diaper in said crotch portion 7 and the pattern diverge from the point 14 it direction towards the side flaps 9 of the rear portion 5. The third elastic means 11c is also preferably arranged between the backsheet 3 and the absorbent body 4 and is at least attached to the backsheet 3. This gives a further sealing from behind of the diaper against the wearer.

The diverging ends of the third elastic means 11c extend towards the upper edge of the rear portion 6 in the area of the side flaps 9, whereby they extend into said projecting portions of the topsheet 2 and the backsheet 3 outside the absorbent body and are attached between these layers. This applies for the belt diaper shown in FIGS. 1 and 2, the all-in-one diaper shown in FIG. 3, and for a pant diaper.

In a preferred embodiment the first, second and the third elastic means 11a, 11b 11c consist of two symmetric elastic means 11. The elastic means 11 essentially extend parallel along the crotch portion 7 and diverge essentially symmetrical from said first point 13 and said second point 14. This embodiment is especially preferred from a production point of view.

The elastic means may consist of elastic ribbons, elastic wire or the like.

Of course, the invention are not limited to the above described and on the drawings shown embodiments, but can be varied within the scope of the claims.

What is claimed is:

1. Absorbent article such as a diaper and an incontinence guard comprising a liquid permeable topsheet, a liquid impermeable backsheet and an absorbent body enclosed therebetween, said article having a front portion, a rear portion and a crotch portion therebetween, whereby the front and rear portion exhibit side flaps, which are intended to attach the article together to a pantlike shape around the waist of the user, characterised in, that it comprises at least one first pre-stressed elastic means attached at least to the backsheet, that said first elastic means is arranged in an essentially V-shaped pattern having the peak of the pattern located to a first point being essentially located on a imagined longitudinal centre line in said crotch portion and that the V-shaped elastic means diverge in the direction from said longitudinal centre line toward the front portion, and that a second elastic means extending from the peak of the V-shaped means and further along the longitudinal centre line at the crotch portion in direction towards the rear portion.

2. Absorbent article according to claim 1, characterised in, a third elastic means is arranged in a second essentially V-shaped pattern having the peak of the pattern located to a second point at the longitudinal centre line on the article on said crotch portion, the pattern diverging from the second point in direction from said longitudinal centre line towards the rear portion.

3. Absorbent article according to claim 1, characterised in, that the first, second and third elastic means comprise two essentially symmetrical elastic means extending essentially parallel along the crotch portion between the first and second point and and diverging essentially symmetrical from said first point and said second point respectively.

4. Absorbent article according to claim 1, and of the kind where the liquid permeable topsheet and the liquid impermeable backsheet has a longer extension in the plane than the absorbent body and extend beyond the edges of the same, wherein the topsheet and the backsheet are mutually joined at said projecting portions, characterised in, that the diverging ends of the first and/or the third V-shaped elastic means extend into said projecting and joined portions of the topsheet and the backsheet at the front portion and the rear portion of the article and are attached between the topsheet and the backsheet.

5. Absorbent article according to claim 4, characterised in, that the diverging ends of the first and/or the third V-shaped elastic means extend to the side flaps of the front and rear portion respectively.

6. Absorbent article according to claim 5, characterised in, that the ends of the first elastic means are connected to the attachment means arranged at the side flaps on the front portion.

7. Absorbent article according to claim 1, characterised in, that the article is an all-in-one diaper, at which the side flaps of the rear and/or front portion exhibits attachment means intended to be attached to the opposite portion.

8. Absorbent article according to claim 1, characterised in, that the article is a pant diaper, at which the side flaps of the rear and front portion respectively are fixedly connected to each other.

9. Absorbent article such as a diaper and an incontinence guard comprising a liquid permeable topsheet, a liquid impermeable backsheet and an absorbent body enclosed therebetween, said article having a front portion, a rear portion and a crotch portion therebetween, whereby the front and rear portion exhibit side flaps, a pair of belt portions are connected to said side flaps of the rear or front portion and which belt portions are intended to be attached around the waist of the user and the side flaps of the opposite portion are intended to be attached to the belt portions by means of attachments means, characterised in, that it comprises at least one first pre-stressed elastic means attached at least to the backsheet, that said first elastic means is arranged in an essentially V-shaped pattern having the peark of the pattern located to a first point being essentially located on a imagined longitudinal centre line in said crotch portion and that the V-shaped elastic means diverge in the direction from said longitudinal centre line in said crotch portion and that the V-shaped elastic means diverge in the direction from said longitudinal centre line toward the front portion.

10. Absorbent article according to claim 9, characterised in, a second elastic means extending from the peak of the V-shaped means and further along the longitudinal centre line at the crotch portion in direction towards the rear portion.

11. Absorbent article according to claim 9, characterised in, a third elastic means is arranged in a second essentially V-shaped pattern having a peak of the pattern located to a second point at the longitudinal centre line on the article on said crotch portion, the pattern diverging from the second point in direction from said longitudinal centre line towards the rear portion.

12. Absorbent article according to claim 9, characterised in, that the first, second and third elastic means comprise two essentially symmetrical elastic means extending essentially parallel along the crotch portion between the first and second point and and diverging essentially symmetrical from said first point and said second point respectively.

13. Absorbent article according to claim 9, and of the kind where the liquid permeable topsheet and the liquid impermeable backsheet has a longer extension in the plane than the absorbent body and extend beyond the edges of the same, wherein the topsheet and the backsheet are mutually joined at said projecting portions, characterised in, that the diverging ends of the first ans/or the third V-shaped elastic means extend into said projecting and joined portions of the topsheet and the backsheet at the front portion and the rear portion of the article and are attached between the topsheet and the backsheet.

14. Absorbent article according to claim 13, characterised in, that the diverging ends of the first and for the third V-shaped elastic means extend to the side flaps of the front and rear portion, respectively.

15. Absorbent article according to claim 14, characterised in, that the ends of the first elastic means are connected to the attachment means arranged at the side flaps on the front portion.

* * * * *